US012295551B2

(12) United States Patent
Weitzner

(10) Patent No.: US 12,295,551 B2
(45) Date of Patent: May 13, 2025

(54) ENDOSCOPE WITH GUIDE

(71) Applicant: Boston Scientific Sciamed, Inc., Maple Grove, MN (US)

(72) Inventor: Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 687 days.

(21) Appl. No.: 17/109,446

(22) Filed: Dec. 2, 2020

(65) Prior Publication Data
US 2021/0076912 A1 Mar. 18, 2021

Related U.S. Application Data

(63) Continuation of application No. 16/668,124, filed on Oct. 30, 2019, now Pat. No. 10,881,279, which is a
(Continued)

(51) Int. Cl.
*A61B 1/00* (2006.01)
*A61B 1/018* (2006.01)
(Continued)

(52) U.S. Cl.
CPC ...... *A61B 1/00154* (2013.01); *A61B 1/00073* (2013.01); *A61B 1/0014* (2013.01);
(Continued)

(58) Field of Classification Search
CPC .. A61B 1/00; A61B 1/005; A61B 1/01; A61B 1/04; A61B 1/05; A61B 1/00073;
(Continued)

(56) References Cited

U.S. PATENT DOCUMENTS

| 3,521,332 A | 7/1970 | Kramer |
| 3,896,793 A | 7/1975 | Mitsui et al. |

(Continued)

FOREIGN PATENT DOCUMENTS

| DE | 42 28 459 A1 | 3/1994 |
| DE | 197 49 687 A1 | 5/1998 |

(Continued)

OTHER PUBLICATIONS

International Preliminary Examination Report issued in International Application No. PCT/IB00/00251 (Publication No. WO 00/54653); date of completion—Apr. 25, 2001.
(Continued)

*Primary Examiner* — Clayton E. LaBalle
*Assistant Examiner* — Fang-Chi Chang
(74) *Attorney, Agent, or Firm* — Bookoff McAndrews, PLLC

(57) ABSTRACT

An instrument for use with an endoscope may include an elongate section configured to move exterior to the endoscope. The elongate section may include a distal end and a proximal end. The instrument may also include an end effector attached to the distal end of the elongate section, and an actuation device attached to the proximal end of the elongate section. The actuation device may be configured to operate the end effector. The instrument may also include a guiding member coupled to the elongate section. The guiding member may be configured to be coupled to an external surface of the endoscope to permit the guiding member to move longitudinally relative to the endoscope. The guiding member may be coupled to the elongate section such that the end effector may extend past a distal end of the endoscope and move in a transverse direction independent of the movement of the distal end of the endoscope.

20 Claims, 5 Drawing Sheets

Related U.S. Application Data continuation of application No. 16/221,696, filed on Dec. 17, 2018, now Pat. No. 10,492,666, which is a continuation of application No. 15/652,417, filed on Jul. 18, 2017, now Pat. No. 10,178,944, which is a continuation of application No. 14/246,283, filed on Apr. 7, 2014, now Pat. No. 9,737,196, which is a continuation of application No. 12/504,122, filed on Jul. 16, 2009, now Pat. No. 8,727,967.

(60) Provisional application No. 61/129,788, filed on Jul. 18, 2008.

(51) Int. Cl.
  *A61B 34/00* (2016.01)
  *A61B 17/00* (2006.01)
  *A61B 17/29* (2006.01)
  *A61B 90/00* (2016.01)

(52) U.S. Cl.
  CPC .............. *A61B 1/018* (2013.01); *A61B 34/72* (2016.02); *A61B 2017/00278* (2013.01); *A61B 2017/00296* (2013.01); *A61B 2017/003* (2013.01); *A61B 2017/0034* (2013.01); *A61B 2017/00477* (2013.01); *A61B 2017/2905* (2013.01); *A61B 2017/2943* (2013.01); *A61B 2090/034* (2016.02)

(58) Field of Classification Search
  CPC . A61B 1/0014; A61B 1/018; A61B 2090/034; A61B 2017/00296; A61B 2017/003; A61B 2017/0034; A61B 2017/00477
  See application file for complete search history.

(56) References Cited

U.S. PATENT DOCUMENTS

| | | |
|---|---|---|
| 4,061,299 A | 12/1977 | Kurosaki |
| 4,245,624 A | 1/1981 | Komiya |
| 4,285,376 A | 8/1981 | Ausnit |
| 4,453,353 A | 6/1984 | Killtop |
| 4,492,230 A | 1/1985 | Sunago et al. |
| 4,646,722 A | 3/1987 | Silverstein et al. |
| 4,669,156 A | 6/1987 | Guido |
| 4,676,229 A | 6/1987 | Krasnicki et al. |
| 4,686,965 A | 8/1987 | Bonnet et al. |
| 4,697,576 A | 10/1987 | Krauter |
| 4,741,326 A | 5/1988 | Sidall et al. |
| 4,793,326 A | 12/1988 | Shishido |
| 4,886,049 A | 12/1989 | Darras |
| 4,935,992 A | 6/1990 | Due |
| 5,025,778 A | 6/1991 | Silverstein et al. |
| 5,037,433 A | 8/1991 | Wilk et al. |
| 5,100,420 A | 3/1992 | Green et al. |
| 5,109,830 A | 5/1992 | Cho |
| 5,171,222 A | 12/1992 | Euteneuer et al. |
| 5,217,001 A | 6/1993 | Nakao et al. |
| 5,226,876 A | 7/1993 | Filipi et al. |
| 5,259,366 A | 11/1993 | Reydel et al. |
| 5,345,937 A | 9/1994 | Middleman et al. |
| 5,383,849 A | 1/1995 | Johlin |
| 5,386,818 A | 2/1995 | Schneebaum et al. |
| 5,423,830 A | 6/1995 | Schneebaum et al. |
| 5,503,616 A | 4/1996 | Jones |
| 5,538,497 A | 7/1996 | Hori |
| 5,607,435 A | 3/1997 | Sachdeva et al. |
| 5,624,380 A | 4/1997 | Takayama et al. |
| 5,662,585 A | 9/1997 | Willis et al. |
| 5,746,692 A | 5/1998 | Bacich et al. |
| 5,749,828 A | 5/1998 | Solomon et al. |
| 5,749,889 A | 5/1998 | Bacich et al. |
| 5,810,776 A | 9/1998 | Bacich et al. |
| 5,820,546 A | 10/1998 | Ouchi |
| 5,873,550 A | 2/1999 | Phillips |
| 5,916,147 A | 6/1999 | Boury |
| 5,944,654 A | 8/1999 | Crawford |
| 5,954,731 A | 9/1999 | Yoon |
| 5,984,932 A | 11/1999 | Yoon |
| 5,997,547 A | 12/1999 | Nakao et al. |
| 6,036,636 A | 3/2000 | Motoki et al. |
| 6,066,090 A | 5/2000 | Yoon |
| 6,071,233 A | 6/2000 | Ishikawa et al. |
| 6,099,464 A | 8/2000 | Shimizu et al. |
| 6,105,216 A | 8/2000 | Opperthauser |
| 6,106,521 A | 8/2000 | Blewett et al. |
| 6,126,633 A | 10/2000 | Kaji et al. |
| 6,179,776 B1 | 1/2001 | Adams et al. |
| 6,352,503 B1 | 3/2002 | Matsui et al. |
| 6,569,085 B2 | 5/2003 | Kortenbach et al. |
| 6,610,007 B2 | 8/2003 | Belson et al. |
| 6,679,872 B2 | 1/2004 | Turovskiy et al. |
| 6,761,685 B2 | 7/2004 | Adams et al. |
| 6,849,042 B2 | 2/2005 | Christopher |
| 7,029,435 B2 | 4/2006 | Nakao |
| 7,060,024 B2 | 6/2006 | Long et al. |
| 7,070,559 B2 | 7/2006 | Adams et al. |
| 7,156,857 B2 | 1/2007 | Pasricha et al. |
| 7,261,728 B2 | 8/2007 | Long et al. |
| 7,951,072 B2 | 5/2011 | Adams et al. |
| 8,444,551 B2 | 5/2013 | Adams et al. |
| 8,932,208 B2* | 1/2015 | Kendale ............ A61B 17/3478 600/176 |
| 10,178,944 B2 | 1/2019 | Weitzner |
| 2003/0036679 A1 | 2/2003 | Kortenbach et al. |
| 2004/0111020 A1 | 6/2004 | Long |
| 2004/0215058 A1 | 10/2004 | Zirps et al. |
| 2004/0230095 A1 | 11/2004 | Stefanchik et al. |
| 2004/0230096 A1* | 11/2004 | Stefanchik ......... A61B 1/00073 600/128 |
| 2004/0230097 A1 | 11/2004 | Stefanchik et al. |
| 2004/0267213 A1 | 12/2004 | Knapp |
| 2005/0065401 A1 | 3/2005 | Saadat et al. |
| 2005/0217198 A1 | 10/2005 | Carraher |
| 2005/0222492 A1 | 10/2005 | Adams |
| 2005/0228224 A1* | 10/2005 | Okada ................ A61B 17/3421 600/153 |
| 2005/0234297 A1 | 10/2005 | Devierre et al. |
| 2005/0267335 A1 | 12/2005 | Okada et al. |
| 2006/0063973 A1 | 3/2006 | Makower et al. |
| 2006/0069304 A1* | 3/2006 | Takemoto .......... A61B 1/00087 600/104 |
| 2006/0079735 A1 | 4/2006 | Martone et al. |
| 2006/0178656 A1 | 8/2006 | Sugita |
| 2006/0264705 A1 | 11/2006 | Adams et al. |
| 2007/0017527 A1 | 1/2007 | Toz |
| 2007/0156019 A1 | 7/2007 | Larkin |
| 2007/0173687 A1 | 7/2007 | Shima et al. |
| 2007/0197862 A1 | 8/2007 | Deviere et al. |
| 2007/0232850 A1 | 10/2007 | Stokes et al. |
| 2007/0239171 A1 | 10/2007 | Stefanchik et al. |
| 2007/0270752 A1 | 11/2007 | LaBombard |
| 2007/0299305 A1 | 12/2007 | Murakami et al. |
| 2008/0125625 A1 | 5/2008 | Belafsky |
| 2008/0132758 A1 | 6/2008 | Stefanchik et al. |
| 2008/0277853 A1 | 11/2008 | Menn |
| 2008/0281299 A1* | 11/2008 | Menn .................. A61B 1/0014 606/1 |
| 2009/0023983 A1 | 1/2009 | Stefanchik |
| 2009/0294600 A1 | 12/2009 | Dodge |

FOREIGN PATENT DOCUMENTS

| | | |
|---|---|---|
| EP | 0 667 126 A1 | 8/1995 |
| EP | 1607037 A1 | 12/2005 |
| EP | 1639936 A1 | 3/2006 |
| JP | H06319682 A | 11/1994 |
| JP | H10146316 A | 6/1998 |
| JP | 63-292935 A | 11/1998 |
| JP | 2003-210399 | 7/2003 |
| JP | 2003-250748 A | 9/2003 |
| JP | 3628742 B2 | 3/2005 |

(56) References Cited

FOREIGN PATENT DOCUMENTS

| JP | 2005-137423 | 6/2005 |
|---|---|---|
| JP | 3806518 B2 | 8/2006 |
| JP | 3810177 B2 | 8/2006 |
| WO | WO 2004/105593 A1 | 12/2004 |
| WO | WO 2007/033379 A2 | 3/2007 |
| WO | WO 2007/135803 A1 | 11/2007 |

OTHER PUBLICATIONS

International Search Report issued in International Application No. PCT/IB00/00251 (Publication No. WO 00/54653); date of completion—Jun. 29, 2000.
Written Opinion issued in International Application No. PCT/IB00/00251 (Publication No. WO 00/54653); date of mailing—Dec. 22, 2000.
English translation of Notice of Reasons for Rejection for Japanese Application No. 2011-518902 mailed Feb. 7, 2014 (4 pages).
Danis, J., "Theoretical basis for camera control in teleoperating", Surgical Endoscopy, 1996, New York, pp. 804-808.

\* cited by examiner

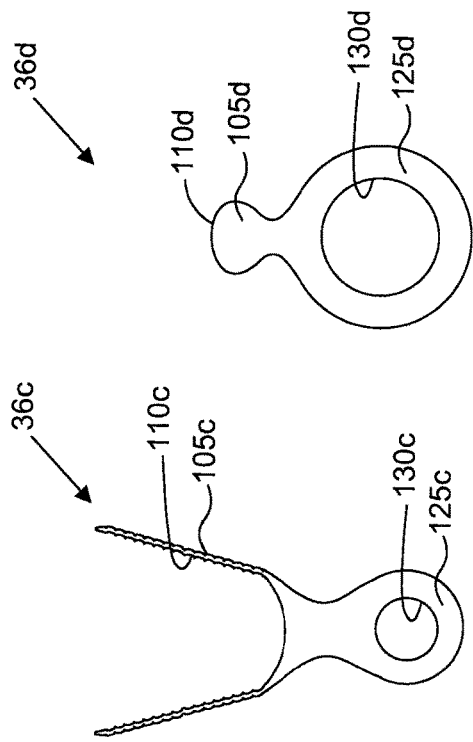
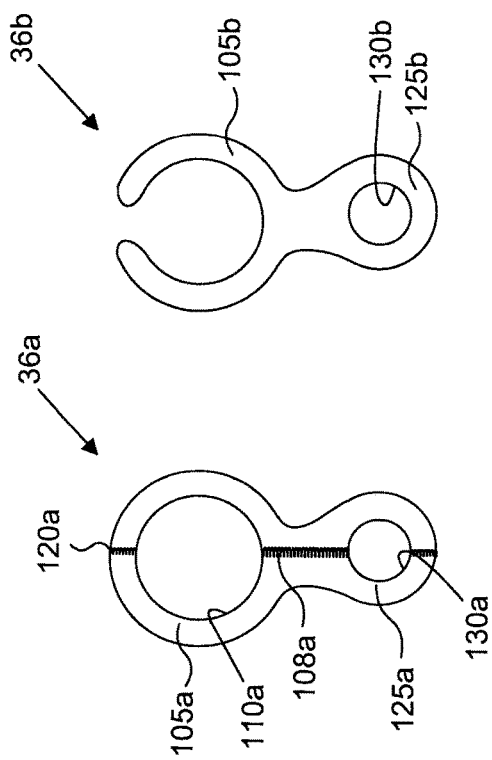
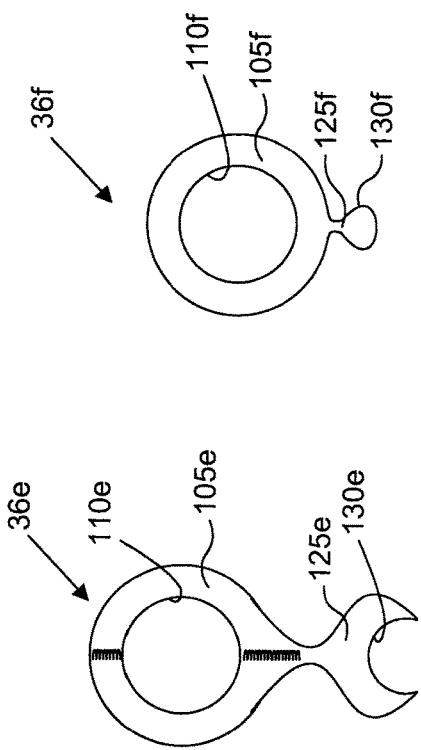
FIG. 5A  FIG. 5B  FIG. 5C  FIG. 5D  FIG. 5E  FIG. 5F

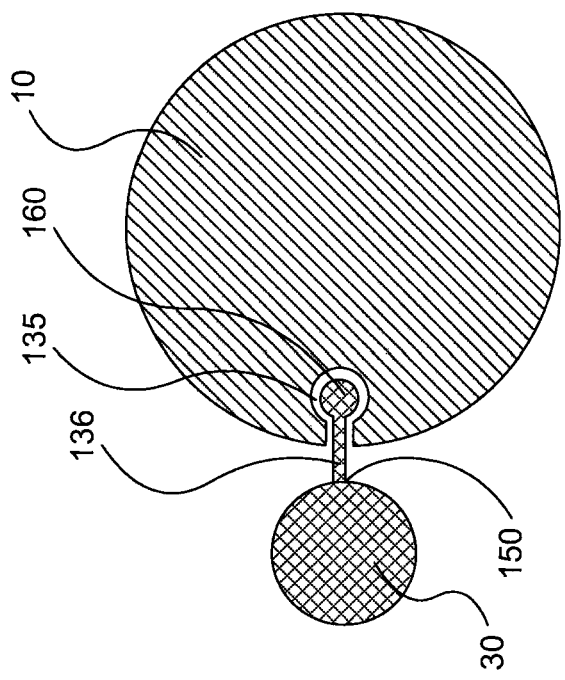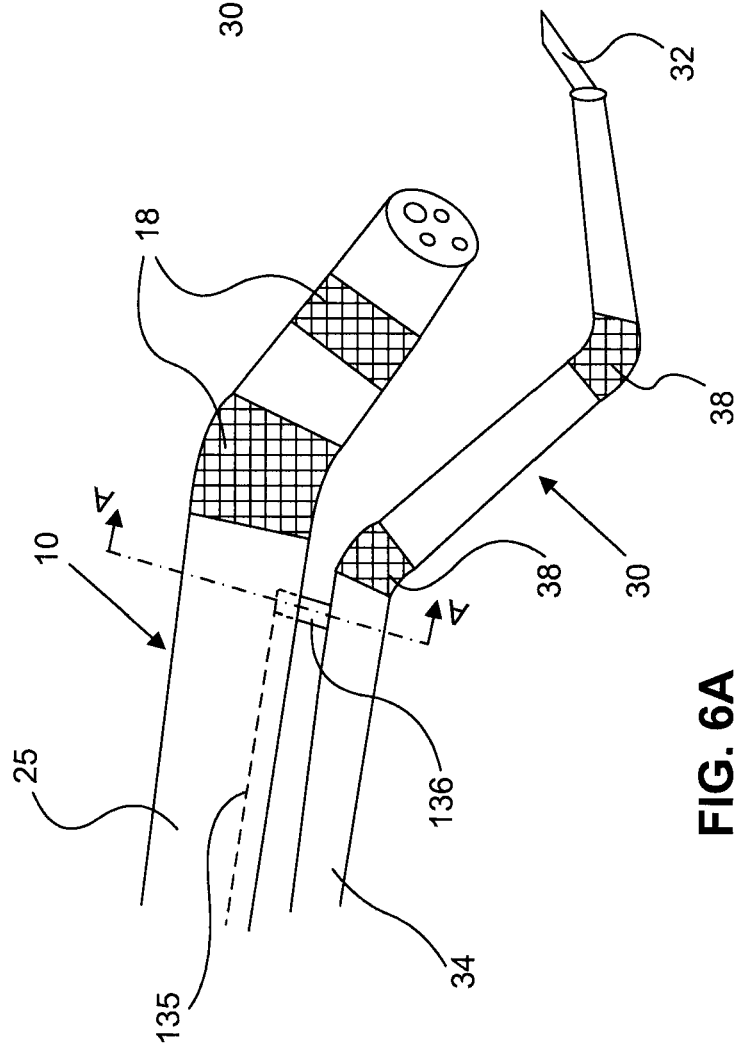

ENDOSCOPE WITH GUIDE

CROSS REFERENCE TO RELATED APPLICATIONS

This application is a continuation of U.S. application Ser. No. 16/668,124, filed on Oct. 30, 2019, which is a continuation of U.S. application Ser. No. 16/221,696, filed on Dec. 17, 2018, now U.S. Pat. No. 10,492,666, issued on Dec. 3, 2019, which is a continuation of U.S. application Ser. No. 15/652,417, filed on Jul. 18, 2017, now U.S. Pat. No. 10,178,944, issued on Jan. 15, 2019, which is a continuation of U.S. application Ser. No. 14/246,283, filed on Apr. 7, 2014, now U.S. Pat. No. 9,737,196, issued on Aug. 22, 2017, which is a continuation of U.S. Application Ser. No. 12/504,122, filed on Jul. 16, 2009, now U.S. Pat. No. 8,727,967, issued on May 20, 2014, which is based upon and claims the benefit of priority under 35 U.S.C. § 119(e) of U.S. Provisional Application No. 61/129,788 to Barry Weitzner, filed on Jul. 18, 2008, each of which is incorporated by reference herein in its entirety.

FIELD OF THE INVENTION

Embodiments of the present invention relate to endoscopes and endoscopic instruments with a guide on an external surface. In particular, exemplary embodiments of the present invention relate to endoscopes and endoscopic instruments that permit delivery of the instruments external to the endoscope. Embodiments of the present invention also covers methods of using such devices.

BACKGROUND OF THE INVENTION

An endoscope is a flexible instrument introduced into the body to examine the inside of the body. In addition to a light source and a camera at the distal end (the end which is inside the body), typical endoscopes may also include a plurality of lumens running therethrough for different tasks. These lumens may include an illumination lumen, viewing lumen, irrigation lumen, aspiration lumen and one or more working lumens. An endoscope is introduced into the body through a body orifice (such as, the rectum or mouth) or a small incision. To minimize human discomfort and maintain flexibility of the endoscope, the diameter of an endoscope is minimized. This restriction on size of the endoscope limits the number and size of the lumens.

Endoscopic instruments, configured to perform different diagnostic and therapeutic tasks, may be delivered to a work site inside the body through the working lumen. From its early use as a purely visual diagnostic tool, endoscopes, along with endoscopic instruments, have grown rapidly to provide an impressive array of therapeutic options. The endoscope can be used for therapeutic purposes in a variety of ways. In some instances, the endoscope serves as a means of access to an appropriate internal body part, allowing the accurate placement of a drug (or other device) on that part, using an endoscopic tool configured for the task. An endoscopic instrument configured for other tasks, for example, a biopsy forceps instrument, may also be delivered to the internal body part through the working lumen. The biopsy forceps instrument may be used to obtain a tissue sample from the body part (for example, the colon). Once the tissue sample has been acquired, the biopsy forceps instrument may be retracted out of the endoscope, and the tissue sample removed from the biopsy forceps instrument.

Endoscopic tools configured for surgical functions (incision, grasping, stitching, cauterizing, etc.) may also be delivered through the working lumens of an endoscope to perform endoscopic surgical procedures. In these instances, the form of the endoscope and the associated instruments may impose physical limits on the surgical task that can be accomplished. These limitations, in some cases, may restrict endoscopic procedures from producing the same anatomical outcome as conventional surgery. Some of these limitations may include the small physical size and number of endoscopic instruments that may be delivered through the working lumen of the endoscope, and the limited maneuverability of the working ends of the endoscopes and endoscopic instruments. There may also be concerns regarding contaminating the working lumens of endoscopes which may result in infections.

Many surgical procedures may require multiple surgical instruments at the working site at the same time. As mentioned earlier, these surgical instruments are typically delivered through the working lumens of the endoscope. The limited number of working lumens in an endoscope limits the number of instruments that can be delivered to the surgical site at a time. Also, while it is often desirable to have larger instruments at the surgical site, the small size of the working lumens limit the size of the tool that can be passed through it. This limitation on physical size also restricts the force that can be applied with the surgical instrument.

A typical endoscope may possess poor maneuverability. The working ends of a typical endoscope may be restricted to movements involving pushing/pulling or limited torque. Similar constraints may apply to instruments introduced via the working lumens. Effective surgery may require that surgical tools possess the ability to, for example, cut and stitch precisely. These requirements may necessitate the precise movement of endoscopic instruments in multiple dimensions. The limited freedom of movement of the working ends of endoscopes and endoscopic tools may hinder these tasks. Ideally, the working ends of endoscopic tools may be configured to move in three dimensions and converge on a given point (a concept referred to as triangulation).

SUMMARY OF THE INVENTION

An embodiment of the invention may include an instrument for use with an endoscope. The instrument may include an elongate section configured to move exterior to the endoscope. The elongate section may include a distal end and a proximal end. The instrument may also include an end effector attached to the distal end of the elongate section, and an actuation device attached to the proximal end of the elongate section. The actuation device may be configured to operate the end effector. The instrument may also include a guiding member coupled to the elongate section. The guiding member may be configured to be coupled to an external surface of the endoscope to permit the guiding member to move longitudinally relative to the endoscope. The guiding member may be coupled to the elongate section such that the end effector may extend past a distal end of the endoscope and move in a transverse direction independent of the movement of the distal end of the endoscope.

Various embodiments of the invention may also include one or more of the following aspects: the elongate section may be configured to rotate the end effector about one or more axes perpendicular to a longitudinal axis of the endoscope; the guiding member may be further configured to permit the elongate section to rotate about a longitudinal axis of the endoscope; the elongate section may be configured to move relative to the guiding member in a direction parallel to a longitudinal axis of the endoscope; the transverse direction may include two mutually perpendicular directions at an angle to a longitudinal axis of the endoscope; the guiding member may be slidably coupled to the elongate section; the guiding member may be removably coupled to the elongate section; the guiding member may be fixedly attached to the elongate section; the guiding member may be configured to interface with a feature on the external surface of the endoscope to stop the movement of the guiding member along the longitudinal axis of the endoscope; the instrument may include the endoscope.

Various embodiments of the invention may also include one or more of the following aspects: the end effector may extend past the distal end of the endoscope by a distance between about 1 cm to 10 cm; a region of the elongate section between the guiding member and the end effector may be configured to move in one or more directions at an angle to a longitudinal axis of the endoscope independent of movement of the distal end of the endoscope; the guiding member may include one or more rings; the one or more rings may include a first ring configured to fit around the elongate section and a second ring configured to fit around the endoscope; the one or more rings may include a hinge configured to permit one or more rings to open; the guiding member may be an integral part of the elongate section and the guiding member may be configured to mate with a mating feature on the external surface of the endoscope to form a male and female mating connection; the mating feature may be a keyway that extends longitudinally along the endoscope; the guiding member may be coupled to the elongate section at a distance of about 11 cm to 20 cm from the end effector.

An embodiment of the invention may include a method of using an endoscopic instrument at a work site internal to a body. The method may include inserting a distal end of an endoscope into the body and locating the distal end of the endoscope proximate to the worksite. The method may also include coupling an endoscopic instrument to an external surface of the endoscope. The endoscopic instrument may have an elongate section and an end effector attached to a distal end of the elongate section. The endoscopic instrument may also include an actuation device attached to a proximal end of the elongate section to operate the end effector. The method may further include moving the endoscopic instrument longitudinal to the endoscope so that the end effector extends a first distance away from the distal end of the endoscope, and operating the endoscopic instrument at the worksite. The operating may include moving the distal end of the elongate section and the end effector in a transverse direction independent of movement of the distal end of the endoscope.

Various embodiments of the invention may also include one or more of the following aspects: the first distance may be between about 1 cm to about 10 cm; coupling the endoscopic instrument may include coupling a guiding member coupled to the elongate section of the endoscopic instrument to the external surface of the endoscope; the guiding member may be coupled to the elongate section at a second distance proximally from the end effector so that when the guiding member is coupled to the external surface of the endoscope, the end effector may extend past the distal end of the endoscope by the first distance to permit the distal end of the elongate section and the end effector to move in one or more directions transverse to a longitudinal axis of the endoscope independent of movement of the distal end of the endoscope; coupling the endoscopic instrument may further include coupling the guiding member to the endoscopic instrument; coupling the guiding member may include positioning a ring of the guiding member about at least a portion of the external surface of the endoscope; coupling the guiding member may include wrapping a flexible section of the guiding member around the external surface of the endoscope; moving the endoscopic instrument may further include rotating the endoscopic instrument around a longitudinal axis of the endoscope; operating the endoscopic instrument may further include rotating the end effector about one or more axes perpendicular to a longitudinal axis of the endoscope; operating the endoscopic instrument may include viewing the end effector through a viewing lumen of the endoscope.

Various embodiments of the invention may also include one or more of the following aspects: coupling a second endoscopic instrument to the external surface of the endoscope, and the second endoscopic instrument may have a second end effector attached to a distal end of a second elongate section; moving the second endoscopic instrument longitudinal to the endoscope so that the second end effector may extend a third distance away from the distal end of the endoscope; positioning the second endoscopic instrument, wherein the positioning may include moving the distal end of the second elongate section and the second end effector in a transverse direction independent of movement of the distal end of the endoscope; positioning the second endoscopic instrument may include moving the distal end of the second elongate section and the second end effector in a transverse direction, independent of movement of the distal end of the endoscope, the distal end of the first elongate section, and the first end effector; operating the endoscopic instrument may include viewing both endoscopic instruments through a viewing lumen of the endoscope; positioning the second endoscopic instrument may include rotating the second endoscopic instrument around a longitudinal axis of the endoscope; positioning the second endoscopic instrument may include rotating the second end effector about one or more axes perpendicular to a longitudinal axis of the endoscope; the third distance may be between about 1 cm to about 10 cm.

An embodiment of the invention may include a medical device including an endoscope with a proximal end, a distal end, and an elongate section connecting the proximal and distal ends. The medical device may also include an endoscopic instrument with an end effector at a distal end, an actuation device at a proximal end, and a shaft coupling the end effector to the actuation device. The endoscopic instrument may extend completely external to the endoscope. The medical device may also include one or more guiding members. The guiding members may be immovably coupled to the shaft and slidably coupled to the elongate section to permit the end effector to move along a longitudinal axis of the endoscope. These guiding members may be coupled to the shaft such that the end effector may extend past the distal end of the endoscope and move in a transverse direction independent of the movement of the distal end of the endoscope.

Various embodiments of the invention may also include one or more of the following aspects: a guiding member closest to the end effector may be positioned between about 11 cm and about 20 cm from the end effector; at least one of the guiding members may be integral with the shaft; the medical device may further include a stop configured to limit the extension of the end effector past the distal end of the endoscope; the stop may be on the endoscope to prevent at least one of the one or more guiding members from sliding past the stop; the shaft may include a flex section in a region proximate the end effector and the flex section may enable the end effector to move in one or more transverse directions relative to the longitudinal axis of the endoscope.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 5A-5F are cross-sectional views of various embodiments of a guide used to attach the endoscopic instrument to the endoscope of FIG. 1.

FIG. 6A is a schematic view of an embodiment of the endoscope of FIG. 1 without a guide.

FIG. 6B is a cross-sectional view of the endoscope of FIG. 6A.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts.

Figure 1:
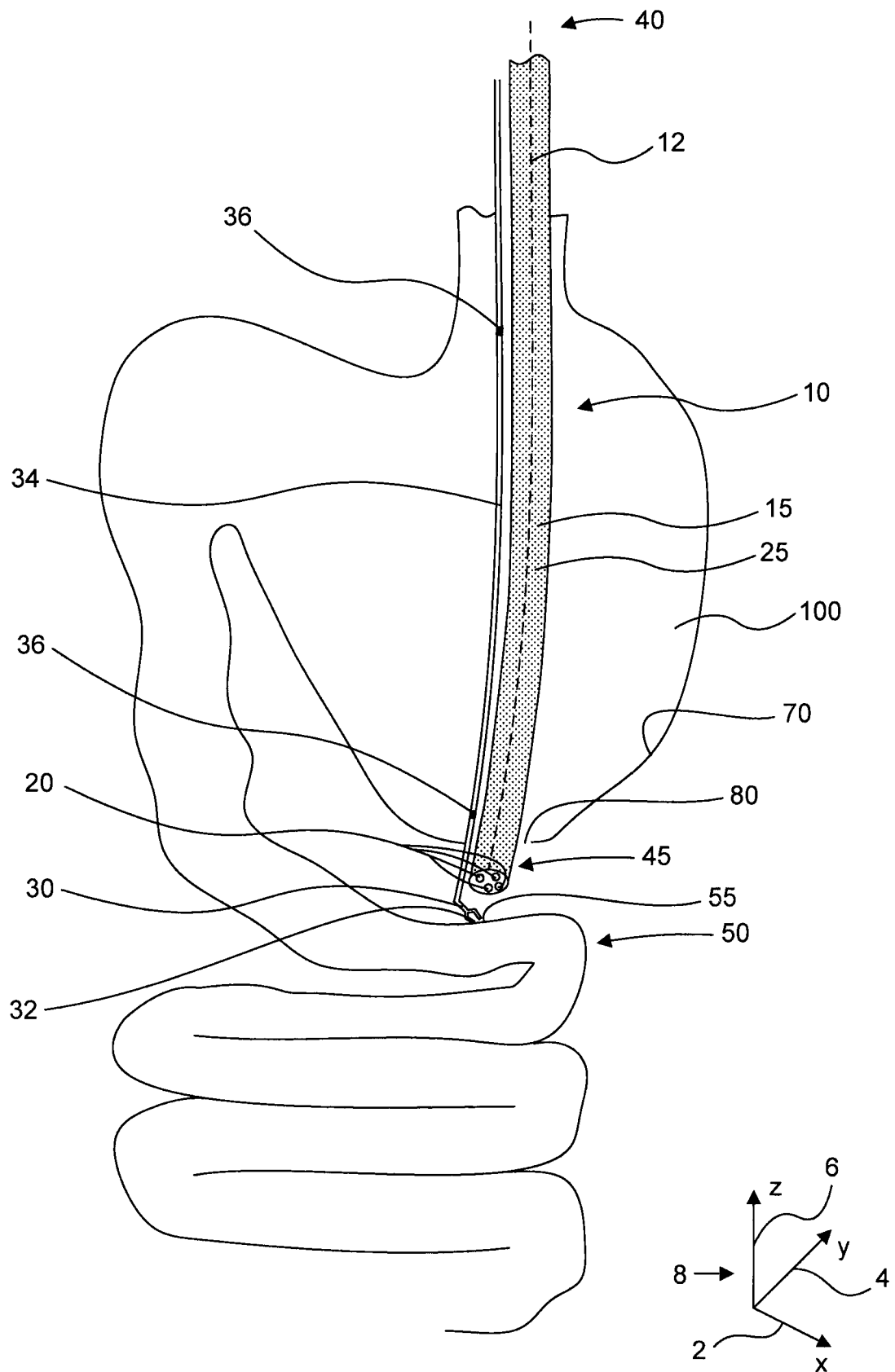
FIG. 1 is a schematic view of an embodiment of an endoscope of the invention performing an exemplary endoscopic surgery.

FIG. 1 depicts an exemplary endoscope 10 performing an exemplary endoscopic surgery, such as transgastric gastrojejunal anastomosis. The endoscope 10 may be inserted into the stomach 100 through the esophagus. The endoscope 10 may make an incision 80 on the stomach wall 70, pass through the incision 80, and operate on a work site 55. The work site 55 could include, for instance, part of the small intestine 50. It should be emphasized that the illustrated application of the endoscope 10 in FIG. 1 is exemplary only, and that the endoscopes of the current disclosure may be applied to any endoscopic application known in the art.

The endoscope 10 may include an elongate member 15 extending between a proximal end 40 and a distal end 45. In the configuration depicted in FIG. 1, the proximal end 40 may include the end of the endoscope 10 external to the body and the distal end 45 may include the end of the endoscope 10 internal to the body. The endoscope 10 may include a curved external surface 25. The endoscope 10 may be constructed of a plurality of materials some of which may be biocompatible. Typically, a part of the endoscope 10 that contacts the internal surfaces of a body may be made substantially of a biocompatible material. In some embodiments, the external surface 25 of the endoscope 10 may be made substantially of a low friction biocompatible material.

The endoscope 10 may include a plurality of lumens 20 running longitudinally therethrough. Each lumen 20 may extend between the proximal end 40 external to the body and the distal end 45 internal to the body. In some embodiments, the longitudinal axis of the lumens may be substantially parallel to the longitudinal axis 12 of the endoscope 10. Additionally, in some embodiments, the lumens 20 may be formed integrally with the endoscope 10 from the proximal end 40 to the distal end 45. The lumens 20 may include one or more of, among others, an aspiration lumen, an irrigation lumen, an illumination lumen, a viewing lumen, and a working lumen. The illumination and viewing lumens may include cables (such as fiber optic cables and light guides) to illuminate the work site 55, and deliver an image of the work site 55 external to the body. These cables may terminate at the distal end 45 of the endoscope 10 at illumination devices (such as bulbs or other solid state devices) and at imaging means (such as lens for a CCD camera). It is also contemplated that the distal end 45 of the endoscope may include a lens and/or other devices that facilitate illumination and viewing of the work site 55.

Any of the lumens may have a substantially circular cross-section. However, it is also contemplated that they may have any suitable shape, size, and/or configuration. For instance, in some embodiments, the shape of the working lumen may be configured to pass an end effector 32 of the endoscopic instrument 30 through it. The irrigation lumen may be configured to facilitate fluid flow therethrough, for example, from the proximal end 40 to the distal end 45. In some embodiments, the proximal end 40 of the irrigation lumen may be configured to be attached to a source of fluid. In some embodiments, the distal end 45 of the irrigation lumen may have a narrow exit. In some embodiments, this narrow exit may be configured in the shape of a nozzle or any other configuration to alter fluid flow.

The aspiration lumen may be configured to facilitate suction and/or fluid flow therethrough. In some embodiments, the flow of fluid through the aspiration lumen and the irrigation lumen may be in substantially opposite directions. For example, fluid may flow through an irrigation lumen towards the distal end 45, while fluid flow through the aspiration lumen may be towards the proximal end 40. In some instances, the aspiration lumen may also be configured to remove biological material from the distal end 45 of the endoscope 10 to the proximal end 40. For instance, a tissue sample along with fluid delivered to the work site 55 via the irrigation lumen may be extracted out of the body through the aspiration lumen. The proximal end 40 of the aspiration channel may be configured to be attached to a source of suction and/or a container configured, for example, to collect the tissue samples. Fluid flow through an irrigation lumen and an aspiration lumen may be independently operated, or their operation may be coordinated to perform a function, such as the extraction of a tissue sample.

One or more endoscopic instruments 30 may protrude from the distal end 45 of the endoscope 10. The endoscopic instrument 30 may pass through (and extend from) the working lumen of the endoscope 10. In some embodiments, the endoscopic instrument 30 may not pass through an internal working lumen, but extend external to, and along side the endoscope 10. For purposes of this disclosure, extending "along side" endoscope 10 includes extending external to the endoscope 10. It is also contemplated that, in some embodiments, some endoscopic instruments may be delivered through the working lumen, while other endoscopic instruments may be delivered along side the endoscope 10. The endoscopic instrument 30 passing along side the endoscope 10 may be secured to external surface 25 of the endoscope 10 using one or more guides 36.

The endoscopic instrument 30 may include a shaft 34 having an end effector 32 attached to the distal end of instrument 30, and an actuation device (not shown) attached to the proximal end of instrument 30. The end effector 32 may include a medical instrument configured to perform a task at the work site 55. In a deployed configuration, the end effector 32 may be internal to the body proximate to the work site 55, and the actuation device may be external to the body.

The end effector 32 may include any medical instrument that may be used in conjunction with endoscope 10. In some embodiments, the end effector 32 may be a purely mechanical medical instrument (for example, biopsy forceps, baskets, graspers, snares, surgical knifes, needles, suturing instruments, etc.), while in others, the end effector 32 may also include devices driven by an electric current (for instance, electric motors, heating elements for cauterizing instruments, a laser lithotripter, etc.). In some embodiments, the end effector 32 may also include sensors to indicate the status of a task. These sensors may include any sensors used in the art. The end effector 32 may be constructed of one or more biocompatible materials.

The actuation device may be configured to operate the end effector 32. Operation of the end effector may include imparting motion to the end effector 32. For instance, the actuation device may be configured to move the end effector 32 in two dimensions along a plane perpendicular to the longitudinal axis 12 of endoscope 10 (that is, along the x-axis 2, y-axis 4 directions of triad 8). In some embodiments, imparting motion to the end effector 32 may include translating the end effector 32 along the x-axis 2, y-axis 4, and z-axis 6 directions (of triad 8). In some embodiments, imparting motion to the end effector 32 may also include rotating the end effector 32 around one or more of the x-axis 2, y-axis 4, and z-axis 6 directions. Operation of the end effector 32 may also include imparting motion to one part of the end effector 32 relative to another. That is, move different parts of the end effector 32 such that the end effector 32 may perform its intended function. For instance, the endoscopic instrument 30 may be intended to perform the function of grasping a tissue sample at the work site 55. The end effector 32 for this purpose may include a pair of jaws rotatably coupled to each other. In such a case, the actuation device may be configured to rotatably move one of the jaws with respect to the other causing the jaws to open or close. The actuation device may be controlled manually, electronically, or by a combination of manual and electronic means. In manual control, an endoscopist (or any human operator) may control the actuation device. In electronic control, the endoscopic instrument 30 may be wholly or partly controlled by a computer (or any electronic control mechanism). In some embodiments, control of the actuation device may be based in part on feedback from sensors incorporated in the endoscopic instrument 30.

The shaft 34 of the endoscopic instrument 30 may include an elongated flexible section made up of one or more parts. The shaft 34 may be configured to operate the end effector 32 in response to actuation of the actuation device. For instance, in the previously stated example of the end effector 32 including a pair of jaws, the shaft 34 may include a wire and a coil with their proximal ends connected to the actuation device and the distal ends coupled to the jaws. Actuation of the actuation device may move the pull wire or the coil relative to the other, causing the jaws to open and close. The actuation device and the shaft 34 may also be configured to allow the end effector to perform more complex tasks. The shaft may also include cables that transmit electric signals to and from the end effector 32. These cables may transmit electric signals (for example, control signals) or electric power (for instance, power to an electric motor or a cauterizing tool) from the actuation device to the end effector 32 (or actuators/motors coupled to the end effector 32). The cables may also transmit signals (for example, sensor signals) from the end effector 32 to the actuation device. The shaft 34 may also be configured to move the end effector 32 in response to actuation by the actuation device. The end effector 32 and the shaft 34 may be made of any biocompatible material.

To deliver an endoscopic instrument 30 with a desired end effector 32 to a work site 55 within the body, the endoscope 10 may be inserted into the body (through a natural anatomical opening or a small incision made for the purpose) such that the distal end 45 of the endoscope 10 is proximate to the work site 55. The endoscopic instrument 30 may now be delivered to the worksite 55 via the endoscope 10. As mentioned earlier, the endoscopic instrument 30 may be delivered via the working lumen within the elongate member 15 of the endoscope 10, or along side the endoscope 10. In embodiments where the endoscopic instrument 30 is delivered via the working lumen, the distal end of the endoscopic instrument 30 may be placed in the working lumen and slid down the elongate member 15 (of the endoscope 10) until the end effector 32 protrudes out of the distal end 45 of the endoscope 10.

In embodiments where the endoscopic instrument 30 is delivered along side the endoscope 10, one or more guides 36 may attach the shaft 34 of the endoscopic instrument 30 to the external surface 25 of the endoscope 10. The guides 36 may be coupled to the shaft 34 at a sufficient distance away from the end effector 32. In certain embodiments, a guide closest to the end effector 32 may be located between about 11 cm and 20 cm from the end effector 32. In some embodiments, the guides 36 may be coupled to a location of the shaft 34 such that, when the endoscopic instrument 30 is attached to the endoscope 10 and the end effector 32 delivered to the work site 55, the end effector 32 may extend past the distal end 45 of the endoscope 10 by a distance sufficient to permit the distal end of the shaft 34 and the end effector 32 to move in the x and y directions. In some embodiments, the guide may be a feature, such as a protrusion incorporated on the shaft 34 of the endoscopic instrument 30 to mate with a mating keyway or a slot on the external surface 25 of the endoscope 10. In such embodiments, these features may be located such that the feature closest to the end effector 32 may be located between about 11 cm and 20 cm from the end effector 32.

To deliver an endoscopic instrument 30 of this embodiment to the work site 55, the guides 36 may be attached to the external surface 25 of the endoscope 10, and the endoscopic instrument 30 slid down the length of the endoscope 10 until the end effector 32 is located at the desired location in the work site 55. As described earlier, in the delivered configuration, the end effector 32 may protrude a sufficient distance beyond the distal end 45 of the endoscope 10. In some embodiments, the end effector 32 may protrude by a distance between about 1 cm to 10 cm. It is contemplated that, in other embodiments of the device, the end effector 32 may protrude by a different distance, for example from 0 cm to 15 cm. In some embodiments, the distance of protrusion of the end effector 32 past the distal end 45 of the endoscope 10 may depend on the focal length of the visual means incorporated in the endoscope 10. The extension of the end effector 32 by a sufficient distance beyond the distal end 45 of the endoscope 10, may enable independent freedom of motion to the instrument (independent from the movement of the distal end 45 of the endoscope 10) at the working end. In such a protruding configuration, the endoscope's eyes (distal end of the endoscope with the visual lumen) may be free to move independent of the hands (end effector 32), thereby enabling the instrument to be used inside the body with improved dexterity.

In some embodiments, the guides 36 may be pre-attached to the endoscopic instrument 30. In some embodiments, the guide may be a feature incorporated on the endoscopic instrument 30 to mate with the external surface 25 of the endoscope 10. In some other embodiments, the guides 36 may be a separate part. In these latter embodiments, guides 36 may be attached to both the external surface 25 of the endoscope 10 and the shaft 34 of the endoscopic instrument (in any order), before the endoscopic instrument 30 is slid down the length of the endoscope 10.

Figure 2:
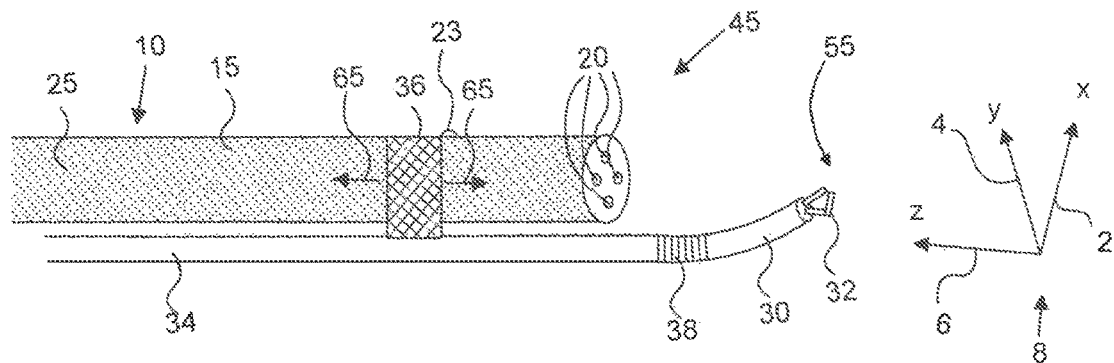
FIG. 2 is a schematic view of a distal portion of an embodiment of the endoscope of FIG. 1.

FIG. 2 shows a schematic of an embodiment of the distal end 45 of an endoscope 10 along with an endoscopic instrument 30 delivered along side the endoscope 10. At least one guide 36 couples the shaft 34 of the endoscopic instrument 30 to the elongate member 15 of the endoscope 10. The guides 36 may be configured to permit relative motion between the endoscope 10 and the endoscopic instrument 30. The direction of this relative motion may be substantially parallel to the longitudinal axis 12 of the endoscope 10, that is, along the z-axis indicated by triad 8. In some embodiments, the guides 36 may be fixedly attached to the endoscopic instrument 30 and movably attached to the external surface 25 of the endoscope 10. Such an attachment may permit the guides 36 to slide on the external surface 25, while being fixedly attached to the endoscopic instrument 30. The texture of the mating surfaces of the guides 36 and the external surface 25 may be such that frictional resistance to sliding may be minimized. In FIG. 2, arrows 65 indicate the sliding of a guide 36 on the external surface 25. When the end effector 32 reaches the desired location at the work site 55, a feature on the endoscope (such as a locking feature, or a stop 23) may prevent further sliding of the guides 36. As depicted in FIG. 2, the stop 23 may be located such that the end effector 32 may protrude the required distance beyond the distal end 45 of the endoscope 10.

In such an embodiment, after the one or more guides 36 are coupled to the external surface 25 of the endoscope 10, pushing the endoscopic instrument 30 into the body may cause the guides 36 to slide on the external surface 25 (as indicated by arrows 65) until the end effector 32 is located at the desired location in the work site 55. In some embodiments, a sensor coupled to the end effector 32 may indicate when end effector 32 is at the desired location. In other embodiments, a tactile indication or a visual indication (including viewing via the endoscope) may be used to indicate when the end effector 32 is at the desired location. In this embodiment, sliding of the guides 36 on the external surface 25 may allow the end effector 32 to move in the direction of the z-axis 6 of triad 8. Actuation of the actuation device may further move the end effector 32 in the x-axis 2 and the y-axis 4 of triad 8. The end effector may, thus, be configured to move in three dimensions at the work site 55.

In some embodiments, movement of the end effector 32 in the x-axis 2 and the y-axis 4 may be accomplished by one or more flex sections 38 of the endoscopic instrument 30. The flex sections 38 may include a section of the shaft 34 that enables the end effector 32 to move in the x-axis 2 and y-axis 4 directions. In some embodiments, one flex section 38 may enable the end effector 32 to move in the x-axis 2 direction and another flex section 38 may enable the end effector to move in the y-axis direction. In some embodiments, the flex sections 38 may also allow the end effector 32 to rotate around the x-axis 2, y-axis 4, and the z-axis 6. As depicted in FIG. 2, the flex sections 38 in some embodiments, may be located in the portion of the endoscopic instrument 30 that protrudes from the distal end 45 of the endoscope 10. Locating the flex sections 38 in this manner may further the ability to move the end effector 32 in a hand like manner, thereby improving dexterity.

The flex sections 38 may include mechanical mechanisms (such as, union joints, gears, linkages, etc.) or electrical devices (motors, stepper motors, actuators, encoders, etc.) that enable the previously described movements of the end effector 32. In some embodiments, flex sections 38 may also include portions of endoscopic instrument 30 of a lower stiffness (than adjacent portions) that enable the described movements. These portions of lower stiffness may include regions of endoscopic instrument 30 made of different materials, sizes, or shapes than adjacent portions. It is also contemplated that flex sections 38 may include smart materials or smart structures that undergo a change in shape or properties in response to an external stimulii (such as, stress, temperature, current, etc.). In some embodiments, these flex sections 38 may also include sensors (or other feedback devices) that may provide a signal indicative of a position of the end effector 32. In some embodiments, the flex sections 38 are discrete sections of the shaft 34 that may be located proximate to the distal end 45 of the endoscope 10. In other embodiments, the flex sections 38 may be more spread out and may encompass a substantial portion of the shaft 34.

Figure 3:
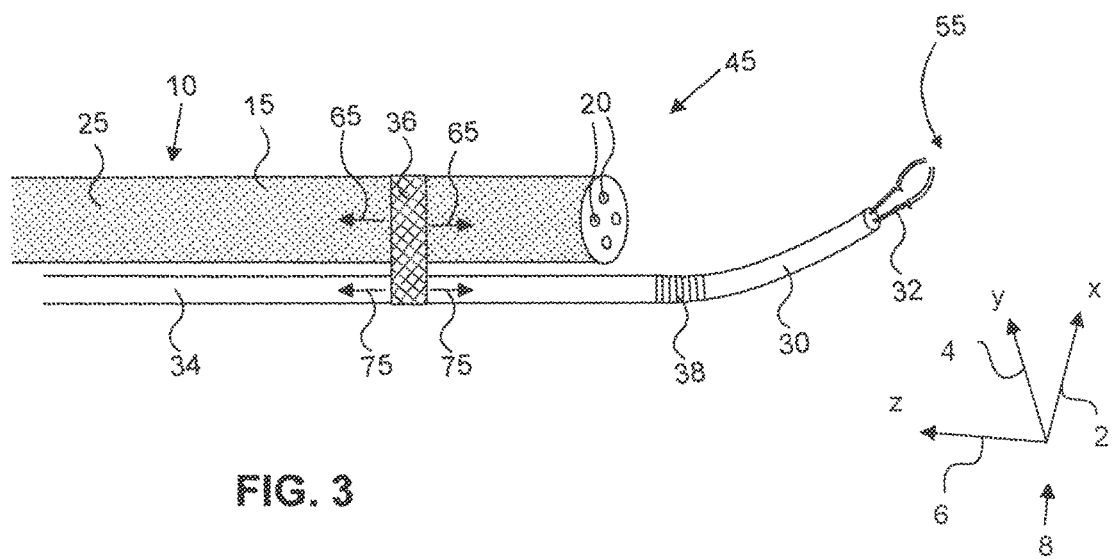
FIG. 3 is a schematic view of a distal portion of another embodiment of the endoscope of FIG. 1.

FIG. 3 shows a schematic of another embodiment of the distal end 45 of an endoscope 10 along with an endoscopic instrument 30 delivered along side the endoscope 10. In these embodiments, the guides 36 may be slidably coupled to both the shaft 34 of endoscopic instrument 30, and the external surface 25 of the endoscope 10. In these embodiments, in addition to the guides 36 sliding on the external surface 25 (movement indicated by arrow 65), the endoscopic instrument 30 may also slide on the guides 36 (movement indicated by arrow 75). In such an embodiment, relative motion between the endoscopic instrument 30 and the endoscope 10 (along the z-axis 6 of triad 8) may be due to a combination of the guides 36 sliding on the external surface 25 (arrow 65), and the endoscopic instrument 30 sliding on the guides 36 (arrow 75). The mating surfaces of sliding parts may be such that only the desired level of frictional resistance is achieved.

In some of these embodiments, the sliding of the guides 36 on the external surface 25 (arrow 65) may occur before sliding of the endoscopic instrument 30 on the guides 36 (arrow 75). In these embodiments, after the guides 36 are coupled to the external surface 25 of the endoscope 10 (and to the shaft 34 of the endoscopic instrument 30, if needed), pushing the endoscopic instrument 30 into the body may cause the guides 36 to slide on the external surface 25 (arrow 65) until the end effector 32 is located at the desired location in the work site 55. In some embodiments, as described with respect to FIG. 2, a stop 23 feature on the endoscope 10 may stop the sliding of the guide 36 when the end effector 32 protrudes the required distance beyond the distal end 45 of the endoscope 10.

Once the end effector 32 reaches the desired location, further movement of the end effector 32 in the z-axis 6 may be accomplished by the endoscopic instrument 30 sliding on the guide 36 (movement indicated by arrow 75). In some embodiments, movement along the z-axis may be accomplished by both the guide 36 sliding on the external surface 25 and the endoscopic instrument 30 sliding on the guide 36 (arrows 65 and 75). Actuation of the actuation device may further move the end effector 32 along the x-axis 2 and the y-axis 4 of triad 8. As described earlier, one or more flex sections 38 may enable the end effector 32 to move along the x-axis 2 and the y-axis 4. The end effector 32 may, thus, be configured to move in three dimensions at the work site 55. In some embodiments, the end effector 32 may also be configured to rotate around the three axes (x-axis 2, y-axis 4, and the z-axis 6).

Figure 4:
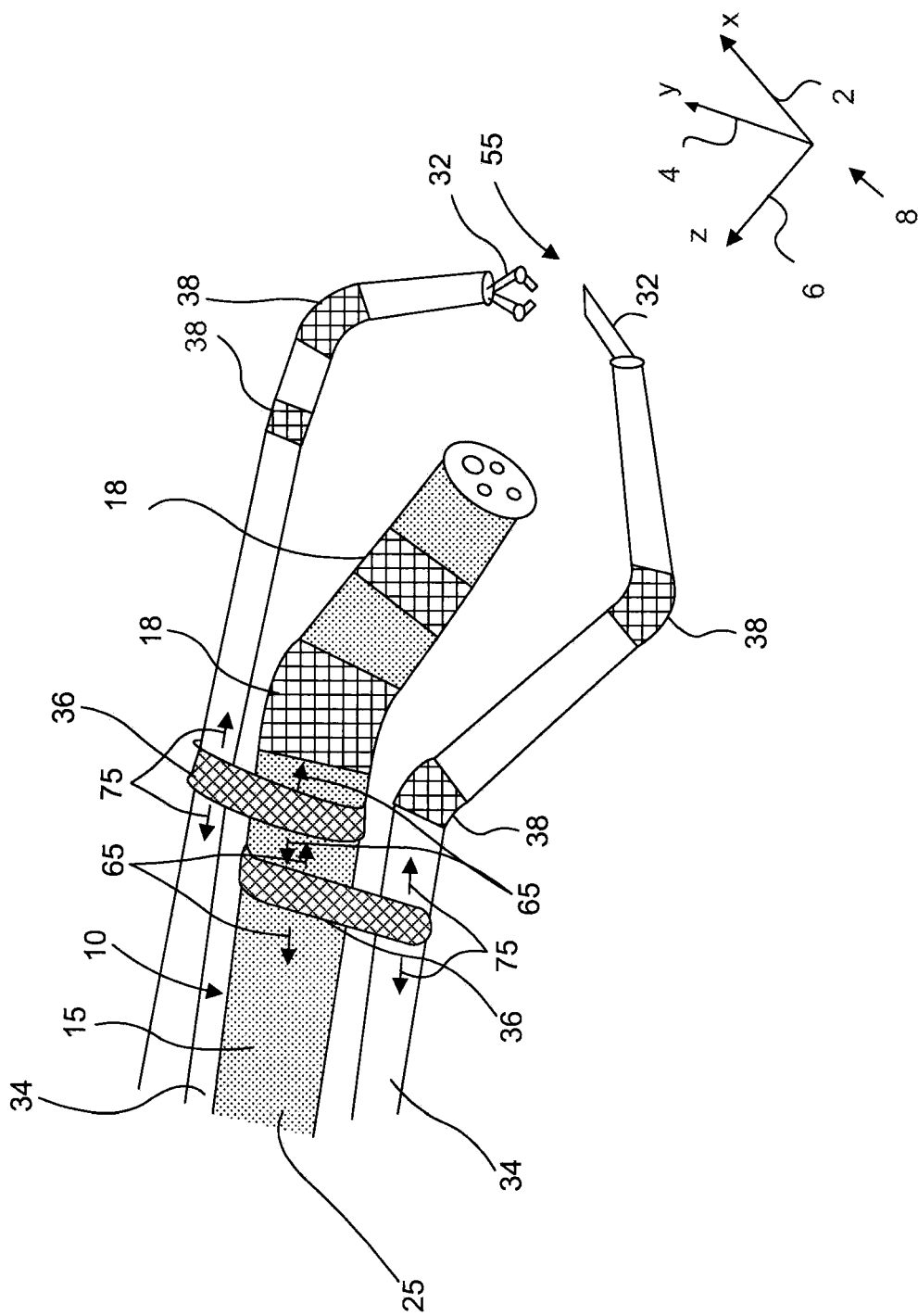
FIG. 4 is a schematic view of a distal portion of another embodiment of the endoscope of FIG. 1.

FIG. 4 shows a schematic of another embodiment of the distal end of an endoscope 10 along with two endoscopic instruments 30 delivered along side the endoscope 10. As mentioned earlier, in addition to the endoscopic instruments 30 depicted in FIG. 4, other endoscopic instruments 30 may be delivered to the work site 55 via the working lumen and/or along side the endoscope 10. The endoscopic instruments 30 may also include guides 36 that may be configured to slide on the external surface 25. In addition, the shafts 34 of the endoscopic instruments 30 may also be configured to slide on the guides 36. The guides 36 of both endoscopic instruments may also be located on the respective shafts such that the both end effectors may extend by a sufficient distance from the distal end of the endoscope 10. As mentioned earlier, extension of the end effectors from the distal end of the endoscope 10 may permit the distal ends of the shafts and the end effectors to move in the x and y directions independent of the distal end 45 of the endoscope 10. In some embodiments, features on the endoscope (such as the stop 23 of FIG. 2) may be positioned to locate the end effectors 32 at a sufficient distance from the distal end 45 of the endoscope 10. Flex sections 38 may also be located to enable the end effectors 32 to move and/or rotate in the x, y, and z axes.

In some embodiments, the x-axis 2, y-axis 4, and the z-axis 6 movements of the end effectors 32 may be coordinated to resemble the movement of a human hand, that is, replicate the elbow and wrist movements of a human hand. Different embodiments of the invention may replicate the movement of the human hand to different levels. For instance, some embodiments or the invention may substantially replicate this human hand movement, while in other embodiments, the x, y and z-axis movement of the end effectors 32 may be less complex. The x, y, and z-axis 2, 4, and 6 movement of the end effector 32 may be controlled by the actuation device. In some embodiments, some of the end effector 32 movements may be substantially controlled by an automated process (for instance, using a computer), while in other embodiments, the end effector 32 movement control may be more manual. Different embodiments of the invention may differ in the level of automated and manual control of the end effector movement. In some embodiments, feedback from sensors incorporated in the end effector 32 (or other parts of the endoscopic instrument 30) may assist control of the end effector 32 movement. Other embodiments may use more visual (for example, provided by the viewing lumen and the endoscopic instrument 30) and/or tactile indications to control the end effector 32 movement.

The endoscope 10 may also include one or more bendable sections 18 that may be configured to provide x and y-axis 2, 4 movement to the distal end 45 of the endoscopic instrument 10. Control of the x and y axis movement of the endoscope distal end may be controlled from the proximal end of the endoscope 10. Similar to the movement of the end effector 32, the x and y-axis movement of the endoscope distal end may be controlled automatically, manually or using a combination of automatic and manual means. In addition to x and y-axis movement, it is also contemplated that in some embodiments, the flex sections 38 may permit the endoscope distal end to move in the z-axis. The endoscope 10 may also include mechanical (gears, links, cables, etc.) and/or electrical devices (motors, actuators, etc.) configured to move the endoscope distal end in the desired direction. It is also contemplated that in some embodiments, some (or all) of the x, y and z-axis 2, 4, 6 movement of the endoscope distal end may be accomplished by incorporation of suitable smart materials (piezoelectric, electro-rheostatic, magneto-rheostatic shape memory alloys, etc.).

In some embodiments, the movement of the endoscope distal end may be coordinated with the movement of the end effector 32. This coordination may be accomplished automatically, manually or using a combination of automatic and manual means. In some embodiments, feedback from sensors may assist in the coordination of the movement. In some embodiments, the movement of endoscope distal end may be based on the movement of the end effector 32 along all three dimensions (x, y and the z-axis 2, 4, 6). In some other embodiments, the endoscope distal end movement may be based on only movement of the end effector 32 along a certain axis (for instance, the x and y-axis 2, 4). This coordinated movement of the end effector 32 and the endoscope distal end may enable the work site 55 to be well lit and visible to an operator at the proximal end 40. In some embodiments, the movement of the endoscope distal end may replicate the movement of a human head (with the viewing lumen representing the eye). As mentioned earlier, in different embodiments of the invention, the endoscope distal end may replicate the movement of the human head to different levels. For instance, some embodiments or the invention may substantially replicate the human head movement, while in other embodiments, the x, y and z-axis movement of the endoscope distal end may be less complex.

The ability of the endoscope distal end and the end effectors 32 to move independently in a coordinated manner may enable an operator to form a working triangle between a left and a right end effector 32, and the endoscope distal end. In some embodiments, this ability may enable the operator to simulate movements at a work site 55 internal to the body like the operator's movements outside the body.

As described above, guides 36 may attach endoscopic instruments 30 to the external surface 25 of the endoscope 10. These guides 36 may be slidably attached to the endoscope 10. These guides may also be fixedly or slidably attached to the endoscopic instrument 30. FIG. 5A through FIG. 5F illustrate cross-sectional views of different exemplary embodiments of the guides 36. The embodiments of the guides 36a-36f depicted in FIG. 5A through 5F may be slidably attached to the endoscope 10 at surface 110a-110f respectively, and slidably or fixedly attached to the endoscopic instrument 30 at surface 130a-130f respectively. The guides 36a-36f may be constructed of one or more biocompatible materials.

In the embodiment shown in FIG. 5A, the guide 36a may include multiple hollow rings 105a, 125a. One ring 105a may fit around the elongate section 15 of the endoscope 10 and another ring 125a may fit around the shaft 34 of the endoscopic instrument 30. Ring 105a may include a hinge 108a and a lock 120a that enables the ring 105a to be opened to fit around the endoscope 10. Once the ring 105a is fit around the endoscope 10, the ring 105a may be closed and the lock 120a engaged. It is also contemplated that, in some embodiments, hinge 108a may include a living hinge or other biasing means so that the ring 105a may be normally closed. In these embodiments, the ring 105a may be held open to fit and snap shut around the endoscope 10. The lock 120a may lock the open sections of the ring 105a to prevent it from accidentally opening. Lock 120a may include any type of locking feature known in the art. Inside surface 110a of ring 105a may be sufficiently lubricious to enable the guide 36a to slide on the external surface 25.

In some embodiments, ring 125a may also be opened and closed to removably fit around the shaft 34 of the endoscopic instrument 30. Embodiments of the ring 125a may also include hinge and lock mechanisms as in ring 105a. Some of these embodiments may also include a live hinge and/or other biasing means as in the case of ring 105a. In other embodiments, the ring 125a may be pre-attached to the shaft 34. In these cases, the endoscopic instrument 30 may have the guides 36a permanently attached to it. In embodiments where the guides 36a are slidably attached to the endoscopic instrument 30, the texture of surface 130a may be tailored to generate only the required amount of sliding friction. In cases where sliding of the guides 36a on the endoscope 10 is desired before sliding of the endoscopic instruments 30 on the guides 36a, the texture of surfaces 110a and 130a may be tailored so that the frictional resistance of surface 110a may be lower than the frictional resistance of the surface 130a.

In the embodiment of the guide 36b shown in FIG. 5B, the ring 105b that fits around the endoscope 10 may be open. In such embodiments, ring 105b may snap around the elongate member 15 of endoscope 10. The material of ring 105b may be sufficiently elastic to snap over the endoscope 10 without breaking or losing its shape.

In the embodiment of the guide 36c shown in FIG. 5C, bendable arms 105c may be bent over the endoscope 10. The material of the bendable arms 105c may be sufficiently inelastic such that they do not spring back open.

In the embodiment of the guide 36d shown in FIG. 5D, ring 105d is a feature that fits on a mating track on the external surface 25 of the endoscope 10. Surface 110d of the feature may also slide on the mating surfaces of the track. This feature can have any shape that will facilitate sliding on a mating track of the endoscope 10.

In the embodiment of the guide 36e shown in FIG. 5E, ring 125e that is attached to the endoscopic instrument 30 may be open. The guide 36e may snap over the endoscopic instrument 30 or may be attached to the endoscopic instrument 30 with a suitable attachment medium. In some embodiments, ring 125e may be integrally constructed with the endoscopic instrument 30.

In the embodiment of the guide 36f shown in FIG. 5F, ring 125f may be a feature that fits on a mating track on the endoscopic instrument 30. It is also contemplated that other embodiments of the guide 36f may mix and match any embodiment of ring 105a-105d depicted in FIGS. 5A-5D with any embodiment of ring 125e-125f depicted in FIGS. 5E-5F.

FIG. 6A shows a schematic of an embodiment of the device where the guide is a feature 136 incorporated on the shaft 34 of the endoscopic instrument 30. FIG. 6B shows a cross-sectional view of the device through plane A-A shown in FIG. 6A. A first end 150 of the feature 136 may be attached to the shaft 34 of the endoscopic instrument 30 and a second end 160 of the feature 136 may mate with a keyway 135 on the external surface 25 of the endoscope 10. The second end 160 may have any shape that is configured to mate with the keyway 135. In some embodiments, the second end 160 and the keyway 135 may have cross-section shaped to resemble a T. In some embodiments, the second end 160 may resemble a spherical knob and the keyway 135 may have a substantially circular cross-section to mate with the spherical knob. It is contemplated that the second end 160 may have any shape, and the corresponding shape of the keyway 135 may include a shape configured to mate with the second end 160.

The endoscopic instrument 30 may include one or more features 136 configured to mate with the keyway 135. The feature 136 may be located between about 11 cm and 20 cm from the end effector 32. In an embodiment where multiple features 136 may be present, the feature 136 located closest to the end effector 32 may be located between about 11 cm and 20 cm from the end effector 32. The distal end of the keyway 135 may also be positioned such that, when the endoscopic instrument 30 is attached to the endoscope 10 and the end effector 32 delivered to the work site 55, the end effector 32 may extend past the distal end 45 of the endoscope 10 by a distance sufficient to permit the distal end of the shaft 34 and the end effector 32 to move in the x and y directions. In some embodiments, this sufficient distance may be between about 1 cm to 10 cm. It is also contemplated that, in other embodiments of the device, the end effector 32 may protrude by a different distance from the distal end 45, for example from 0 cm to 15 cm.

To illustrate applications of the disclosed endoscope 10 and the endoscopic instrument 30, exemplary methods of use will now be described. The distal end 45 of an endoscope 10 may be inserted through the mouth of a patient. The endoscope 10 may be gently pushed down the patient's esophagus until the distal end 45 of the endoscope 10 is proximate to a work site 55 (for instance, the wall of the stomach). Proximity of the distal end 45 to the work site 55 may be identified by viewing an image from a viewing lumen of the endoscope 10, for example, displayed on a monitor. An endoscopic instrument 30 with an appropriate end effector 32 (for instance, a forceps) including pre-attached guides 36 on the shaft 34 may be snapped over the external surface 25 of the endoscope 10. The endoscopic instrument 30 may now be gently pushed into the patient's body (along the z-axis 6 indicated in FIG. 4) along side the endoscope 10. During insertion, it is preferable that the end effector 32 of the endoscopic instrument 30 be in a configuration so as not to damage internal tissue of the participant. For example, the forceps jaws may be closed and/or retracted within a sheath. During instrument insertion, the guides 36 may slide on the external surface 25 of the endoscope 10 to deliver the end effector 32 to the distal end 45 of the endoscope 10. At the distal end 45, one or more guides 36 may be blocked from further travel by a stop 23 on the external surface 25 of the endoscope 10. The endoscopic instrument 30 may be rotated around the longitudinal axis 12 of the endoscope 10 to locate the end effector 32 at a suitable position.

The end effector 32 may now be moved in the x and y-axis 2, 4 directions to bring the end effector 32 into the field of view of the visual lumen, by actuating the actuation device of the endoscopic instrument 30. The end effector 32 may also be moved further in the z-axis 6 direction by gently pushing down the endoscopic instrument 30. Further movement of the end effector 32 in the z-axis 6 direction may be accomplished by the endoscopic instrument 30 sliding on the guides 36. Once the end effector 32 is suitably located at the work site 55, the actuation device may be actuated to operate the end effector 32 as desired (for instance, to open and shut the jaws of the forceps). The actuation device may be actuated to grasp and remove a tissue sample for biopsy. The endoscopic instrument 30 may be slowly pulled out of the body to extract the tissue sample for laboratory tests.

In another embodiment, once the forceps described in the previous embodiment is located at the work site 55, another endoscopic instrument 30 with a suitable end effector 32 (for instance, a cautery end effector) may also be dispatched to the work site 55. The endoscopic instrument 30 with a cautery end effector may be attached to the external surface 25 of the endoscope 10 by snapping a removable guide 36 around the shaft 34 of the endoscopic instrument 30 and the external surface 25 of the endoscope 10. The cautery end effector may also be positioned as desired in the work site 55 by moving the end effector in the x, y and z-axis direction using the actuation device. More end effectors 32 may be similarly dispatched to the work site 55 if desired. Dispatching the end effectors 32 to the work site 55 external to the endoscope 10 may allow the diameter of the endoscope 10 to be reduced. Reducing the diameter of the endoscope 10 may reduce patient discomfort and increase the flexibility of the endoscope 10 by reducing its flexural rigidity. Since the size of the end effector 32 dispatched external to the endoscope 10 may be independent of the cross-sectional size of the working lumen, increasing end effector size may not increase the endoscope diameter. Dispatching end effectors 32 external to the endoscope may also reduce the likelihood of contamination of the working lumens, and resultant spread of disease.

When all the required end effectors 32 are positioned as desired, the end effectors 32 and the endoscope distal end may be moved in the x, y, and z-axis directions by controlling the flex sections 38 of the endoscopic instruments 30, and the bendable sections 18 of the endoscope 10. Controlling the individual movements of the end effectors 32 and the endoscope distal end in a coordinated manner, may allow an operator to form a working triangle between the surgical tools (cautery and forceps end effectors), and the scope's eyes (endoscope distal end). The control and dexterity that may be permitted by the ability to move the surgical instruments in all three dimensions, independently and precisely, may allow an operator to use the instruments within the body, as he may use corresponding instruments in conventional surgery external to the body.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

We claim:

1. An assembly comprising:
   a first instrument having a first shaft;
   a second instrument having a second shaft;
   a third instrument having a third shaft;
   a first guide having:
      a first portion including a first hinged opening configured to transition from an open configuration to a closed configuration, wherein, in the open configuration, the first shaft is insertable into the first portion, and wherein, in the closed configuration, the first shaft is coupled to the first portion; and
      a second portion configured to be coupled to the second shaft of the second instrument; and
   a second guide having:
      a third portion configured to be coupled to the first shaft of the first instrument; and
      a fourth portion configured to be coupled to the third shaft of the third instrument,
   wherein each of the first instrument, the second instrument, the third instrument, the first guide, and the second guide are longitudinally movable relative to one another.

2. The assembly of claim 1, wherein the third portion of the second guide includes a second hinged opening configured to transition from an open configuration to a closed configuration, wherein, in the open configuration, the first shaft is insertable into the third portion, and wherein, in the closed configuration, the first shaft is coupled to the third portion.

3. The assembly of claim 1, wherein the first hinged opening is biased to the closed configuration.

4. The assembly of claim 1, wherein the first portion further includes a lock for securing the first hinged opening in the closed configuration.

5. The assembly of claim 1, wherein the first portion of the first guide is slidably coupled to the first shaft.

6. The assembly of claim 1, wherein the second portion of the first guide is slidably coupled to the second shaft.

7. The assembly of claim 1, wherein the first guide includes a ring, wherein the first hinged opening extends entirely through a first portion of a wall of the ring and wherein the first hinged opening extends at least partially through a second portion of the wall of the ring, wherein the first portion of the wall of the ring is opposite the second portion of the wall of the ring.

8. The assembly of claim 1, wherein the second guide is proximal of the first guide.

9. The assembly of claim 1, wherein the first guide includes a first lock.

10. An assembly comprising:
    a medical device having a proximal end, a distal end, and a length extending between the proximal end and the distal end, wherein the medical device includes a continuous first track formed on an outer surface thereof; and
    a first instrument having a first shaft and an end effector, wherein the first instrument is configured to be slidably coupled to the first track by only a first protrusion incorporated into and protruding from a surface of the first shaft that mates with the first track, wherein, when the first instrument is coupled to the medical device such that a distal end of the first instrument is distal to the distal end of the medical device, the first protrusion is disposed within the first track, and an entirety of the first protrusion is proximal to a steerable section near the distal end of the medical device.

11. The assembly of claim 10, wherein the medical device further comprises a second track formed on the outer surface thereof, the assembly further comprising:
    a second instrument having a second shaft, wherein the second instrument is configured to be slidably coupled to the second track by a second protrusion that mates with the second track.

12. The assembly of claim 10, wherein the first protrusion has a circular-shaped cross section or a T-shaped cross-section.

13. The assembly of claim 10, wherein the first track is a keyway that extends radially into the medical device from the outer surface of the medical device.

14. The assembly of claim 10, wherein the first instrument includes a handle and wire that extends from the handle and through the first shaft for actuating the end effector.

15. An assembly comprising:
    a medical device having a proximal end, a distal end, a length extending between the proximal end and the distal end, and a steerable section near the distal end, wherein the medical device includes a feature disposed on an external surface of the medical device;

a first instrument having a first shaft; and a first guide coupled to the first shaft, wherein the first guide is configured to removably couple the first shaft to the external surface of the medical device, wherein the first guide includes a ring configured to extend around the external surface of the medical device, wherein the feature is configured to stop distal movement of the first guide by interacting with the ring, such that a distal end of the first instrument extends distally beyond the distal end of the medical device when an entirety of the first guide is disposed proximally of the steerable section of the medical device when the first guide interacts with the feature of the medical device.

16. The assembly of claim 15, further comprising:

a second instrument having a second shaft; and a second guide coupling the second shaft to the external surface of the medical device, wherein the first guide and the second guide are discrete elements, separate from one another, wherein the first guide is removable from each of the medical device and the first instrument, and wherein the second guide is removable from the medical device and the second instrument, wherein the second guide is configured such that a distal end of the second instrument extends distally beyond the distal end of the medical device when an entirety of the second guide is disposed proximally of the steerable section of the medical device.

17. The assembly of claim 16, wherein the ring of the first guide is a first ring and the second guide includes a second ring, and wherein the second ring is disposed around the external surface of the medical device.

18. The assembly of claim 15, wherein the external surface of the medical device includes a track, and wherein the first guide includes a feature that mates with the track.

19. The assembly of claim 15, wherein the first guide is proximal of a steerable section of the first instrument.

20. The assembly of claim 15, wherein the medical device is an endoscope.

* * * * *